(12) United States Patent
Sochor

(10) Patent No.: US 7,736,191 B1
(45) Date of Patent: Jun. 15, 2010

(54) IMPLANTABLE CONNECTOR WITH PROTECTED CONTACTS

(76) Inventor: Jerzy Roman Sochor, 425 Costa Mesa Ter Apt D, Sunnyvale, CA (US) 94085

( * ) Notice: Subject to any disclaimer, the term of this patent is extended or adjusted under 35 U.S.C. 154(b) by 0 days.

(21) Appl. No.: 12/467,805

(22) Filed: May 18, 2009

Related U.S. Application Data

(60) Provisional application No. 61/056,086, filed on May 27, 2008.

(51) Int. Cl.
*H01R 24/04* (2006.01)
(52) U.S. Cl. ............... 439/668; 439/909; 600/378; 607/116
(58) Field of Classification Search .......... 439/668, 439/909; 600/378; 607/116, 37, 38, 57, 607/137
See application file for complete search history.

(56) References Cited

U.S. PATENT DOCUMENTS

| | | | | |
|---|---|---|---|---|
| 6,415,168 | B1* | 7/2002 | Putz | 600/378 |
| 6,662,035 | B2* | 12/2003 | Sochor | 600/378 |
| 7,402,083 | B2* | 7/2008 | Kast et al. | 439/660 |
| 7,422,487 | B2* | 9/2008 | Osypka | 439/668 |
| 7,425,142 | B1* | 9/2008 | Putz | 439/138 |
| 7,553,193 | B2* | 6/2009 | Kast et al. | 439/660 |

* cited by examiner

*Primary Examiner*—Gary F. Paumen

(57) ABSTRACT

An implantable connector electrically connects multi-conductor leads to an implantable medical device such as a neurostimulator. The connector is assembled directly into a hermetic feedthrough of the implantable device and utilizes the feedthrough housing as a sustaining structure for connector clamping. The receptacle contacts detachably connect proximal lead contacts to corresponding feedthrough pins, which provide pass-through connections to electronic circuitry contained in a hermetically sealed case. The receptacle contact has resilient contact tines designed to engage a corresponding lead contact in a sliding manner. The receptacle contact is integrated with a contact guard which protects the receptacle contact from inadvertent handling damage. The contact guard is substantially more rigid than the resilient contact to resist deformation. The contact guard protectively shields the receptacle contact tines and prevents unintended contact tine excursion. In one embodiment, the contact guard is pre-attached to the receptacle contact prior to joining to the feedthrough pin. In another embodiment, the contact guard is an integral part of the feedthrough pin. Numerous embodiments with contact preload are provided.

21 Claims, 15 Drawing Sheets

IMPLANTABLE CONNECTOR WITH PROTECTED CONTACTS

CROSS-REFERENCE TO RELATED APPLICATION

This application claims priority of provisional patent application Ser. No. 61/056,086, filed 2008 May 27 by the present inventor.

BACKGROUND

Prior Art

A typical implantable electronic device, such as a cochlear implant, cardiac pacemaker, or a neurostimulator, has electronic circuitry (electronics) that is contained in a hermetic housing or case. The device has attached at least one multi-conductor lead that has sensing and/or stimulating electrodes on its end which is distal from the device and which is implanted in the tissue targeted for therapy (cochlea, heart muscle, particular area of brain, etc.). Other leads may connect the device to additional implantable system components, such as drug delivery devices, implantable inductive coils (for energy delivery to the device and/or data communication with the device), or power sources, which may have to reside in a more accessible body area for easier charging and/or replacement.

It is preferable that the implantable leads and devices be detachable so that either a device or leads can be implanted or explanted independently. This functionality is provided by a connector on the exterior of the device which connects the proximal (near-device) end of the lead to the device. The connector connects lead contacts on the lead's proximal end and provides pass-through connections to the device's electronics across a hermetic feedthrough so that the hermeticity of the device's case is not compromised, i.e., the electronics remains sealed from the body fluids and moisture. It is further desirable that the connections have a small size, can provide a rapid connection and disconnection without special tools, and allow multiple connect and disconnect cycles without loss of function.

As the implantable medical devices and systems become more capable and the number of the leads and the lead contact count increase, there is a need for small but robust connectors to make reliable connections to devices or components of the implantable system. In a connection-intensive device the connector may constitute a significant proportion of the device's volume; thus a smaller connector leads to a smaller device. The small size is especially important for devices such as neural and cochlear stimulators which are implanted in the cranium, both for medical reasons (a smaller cranial cavity needs to be created) and for aesthetic advantages. In such cases, it may be desirable to build the connector interface directly into the device's feedthrough housing cavity so that receptacle contacts are co-located with the feedthrough pins.

My U.S. Pat. No. 6,662,035 (2003) shows a feedthrough-based connector design intended for a device implantable beneath the scalp. This patent teaches how to implement reliable direct metal-to-metal connections between lead contacts and the corresponding feedthrough pins.

The connector uses C-shaped compressible contacts attached directly to the feedthrough pins. Clamping of the connector cover with a screw forces the lead's proximal contacts, pre-inserted into an interposer (seal), against the compressible contacts, thus completing connection of the lead electrodes with the device's electronics.

The compressible spring contacts extend above the exterior (outwardly facing) surface of the dielectric substrate and thus are susceptible to a handling damage (e.g., due to unintended contact with a human hand, a surgical tool, or a mismated component) if made too fragile. On the other hand, a robust compressible spring contact (for adequate handling integrity) and a relatively large seal increase burden on connector clamping hardware, requiring a substantial clamping cover and screw.

In general, a smaller contact size and lower connector clamping forces are desirable in order to reduce the size of the connector. However, the smaller contact must have an adequate handling integrity and provide resilient deflection capability to accommodate assembly tolerances and to assure an adequate deflection reserve for repeated mating.

Another issue in miniature implantable connectors is protection of the implantable leads from handling damage, especially during intra-operative attachment of the leads to the connector. In order to protect the miniature implantable lead, the lead's proximal or connector end may need to be pre-inserted into a lead-receiving connector component without significant insertion force. A significant clamping force is then applied to engage the lead contacts with the compressible contacts of the connector. When compressible contacts are used, a sustained clamping force is required to maintain contact engagement.

The sustaining clamping force can be reduced if a receptacle contact with opposing contact tines is used to engage the sides of a lead contact in a sliding manner. Such contact is self-sustaining (i.e., the normal forces on the opposing contact tines are balanced and supported by the contact body) and therefore does not rely on clamping force to maintain the contact forces. A sliding contact engagement can be completed without application of clamping hardware and can be used to secure the leads in the connector during connector assembly. (In general, it is not feasible to pre-engage leads with compressible contacts since, in the absence of the sustaining clamping force, the compressible contacts will simply push back the lead.)

Mating tolerances are smaller and generally more predictable in a sliding engagement. The variation in the amount of compressible contact deflection depends on the dimensional tolerances of compressible contact height, lead contact size, and dimensions of the seal and clamping hardware components. In contrast, the variation in the sliding contact deflection depends mainly on the dimensional tolerances of the contact gap between the tines and the size (typically diameter) of the sliding contact.

SUMMARY

The present device, in one aspect, addresses the need for improved small implantable connectors built directly on a hermetic feedthrough of an implantable electronic device, such as a cochlear implant, a neurostimulator, a pacemaker, a pain-control device, and the like.

The connector in this aspect uses a protected receptacle contact integrated with the feedthrough pin and employs the feedthrough housing as the sustaining structure for connector assembly and clamping.

The contact system consists of a receptacle contact for slidably engaging a lead contact, and a means to position, secure, protect, and preload the receptacle contact (the contact guard). The receptacle contact is generally U- or W-shaped and has two free-ended tines for slidably engaging the sides of a lead contact. Upon engagement, the contact is self-sustaining and therefore does not rely on the clamping means to maintain contact forces.

The receptacle contact is structurally integrated with the contact guard, which defines the mating lead contact seating envelope and protects the receptacle contact from an accidental damage. The contact guard protectively shields the receptacle contact's spring tines, thus preventing their inadvertent deformation and, preferably, maintains desirable contact gap by preloading the receptacle contact tines. A small but robust contact system is possible with the use of the contact guard. The contact guard protection enables use of a miniaturized contact which would otherwise be impractical due to susceptibility of the miniature contact to handling damage (e.g., from a mismated lead-seal assembly or inadvertent contact with a surgical tool).

The receptacle contact self-sustains contact normal forces; this reduces the structural loading required to support contact mating forces and therefore the size of the clamping hardware components. For example, the low clamping force enables use of small-sized clamping cover and space-efficient retention clips, which can be easily installed and removed without use of tools. (A provision for use of a simple screwdriver or a temporary external tool is also provided.)

The contact guard can be an integral part of the feedthrough pin or a separate component joined to the feedthrough pin. In some contact embodiments the contact guard can also provide contact tine preloading, which helps to reduce contact engagement force and assures consistent contact normal force.

The connector is advantageous for connecting iso-diametric leads with tubular or ring contacts but can also be adapted to connect to non-circular contact profiles (e.g., lead contacts with flat or blade-like mating sides). In order to protect the miniature implantable leads, a lead proximal end is first inserted into a seal without encountering significant resistance. Once the lead is protected by the seal, the lead-seal assembly is subsequently lightly pressed into a feedthrough cavity which retains and aligns the lead-seal assembly for the remaining steps of connector assembly and pressurization.

DRAWINGS

DRAWINGS-REFERENCE NUMERALS

Figure 1A:
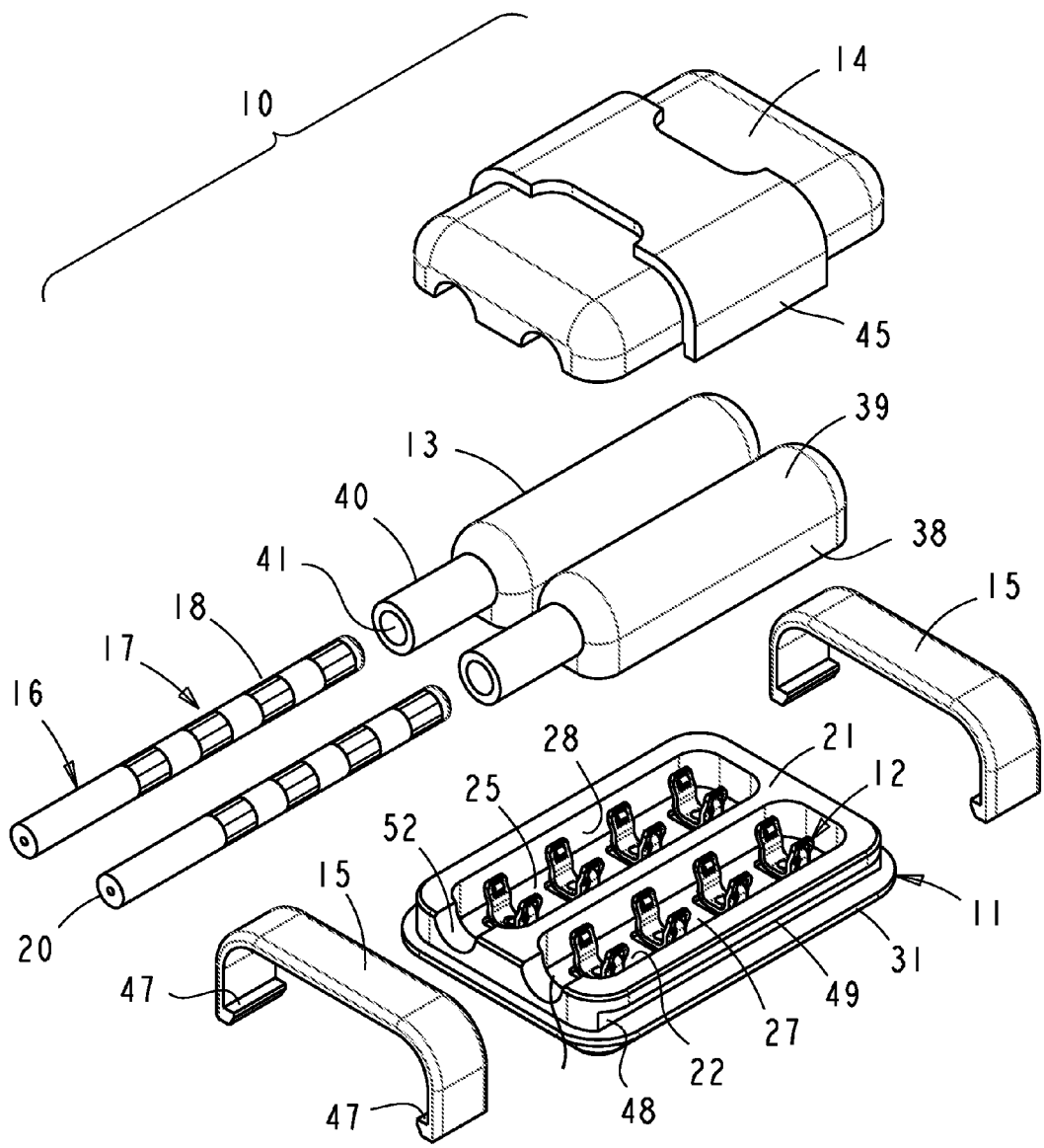
FIGS. 1A and 1B are exploded perspective views, top and bottom views respectively, of a connector for separably connecting multi-conductor leads to an implantable device.

| 10 | connector | 11 | feedthrough |
|----|-----------|----|-------------|
| 12 | contact assembly | 13 | seal |
| 14 | clamping cover | 15 | clip |
| 16 | lead | 17 | proximal end, lead |
| 18 | lead contact | 19 | conductor, lead |
| 20 | body, lead | 21 | housing, feedthrough |
| 22 | dielectric substrate | 23 | feedthrough pin |
| 24 | braze | 25 | exterior side, dielectric substrate |
| 26 | interior side, dielectric substrate | 27 | cavity, feedthrough |
| 28 | inside wall, feedthrough | 29 | head, feedthrough pin |
| 30 | case, hermetic | 31 | welding flange, feedthrough |
| 35 | receptacle contact | 36 | contact guard |
| 37 | bottom, seal | 38 | side perimeter, seal |
| 39 | top, seal | 40 | sleeve, seal |
| 41 | lumen, seal | 42 | aperture, seal |
| 43 | pocket, cover | 44 | channel, cover |
| 45 | extended wall, cover | 46 | location, cover protrusion |
| 47 | latch, clip | 48 | undercut, feedthrough housing |
| 49 | side wall, feedthrough housing | 50 | relief, cover |
| 51 | mid-point, feedthrough side | 52 | channel, feedthrough housing |
| 55 | contact tine, receptacle contact | 56 | mid-section, receptacle contact |
| 57 | weld line | 58 | arm, contact guard |
| 59 | base, contact guard | 60 | mating end, contact |
| 61 | cutout, contact guard arm | 62 | tip, contact guard arm |
| 63 | weld line | 64 | mid-point, contact guard base |
| 65 | hole, contact | 66 | hole, contact guard |
| 67 | edge, cutout | 68 | outline, lead contact |
| 69 | tangent line | 70 | contact |
| 71 | contact guard | 72 | feedthrough pin |
| 73 | head, feedthrough pin | 74 | weld line |
| 75 | mid-section, receptacle contact | 81 | base, contact guard |
| 82 | weld line | 90 | contact assembly |

-continued

| | | | |
|---|---|---|---|
| 91 | receptacle contact | 92 | contact guard |
| 93 | head, feedthrough pin | 94 | feedthrough pin |
| 95 | base, contact guard | 96 | weld line |
| 97 | slot, feedthrough pin | 98 | outside edge, contact guard |
| 99 | edge, feedthrough pin | 100 | top surface, feedthrough pin |
| 101 | weld line | 110 | receptacle contact |
| 111 | contact guard | 112 | weld line |
| 113 | head, feedthrough pin | 114 | feedthrough pin |
| 115 | weld line | 116 | slotted side, contact guard |
| 117 | preload edge | 130 | contact assembly |
| 131 | receptacle contact | 132 | contact guard |
| 133 | head, feedthrough pin | 134 | feedthrough pin |
| 135 | mid-section, contact | 136 | contact tine |
| 137 | base, contact guard | 138 | weld line |
| 139 | slot, feedthrough pin head | 140 | flat side, slotted head |
| 141 | step, contact guard | 142 | edge, contact guard |
| 143 | edge, feedthrough pin | 144 | side arm, contact guard |
| 145 | slot, contact guard | 146 | preload edge |
| 150 | receptacle contact | 151 | feedthrough pin |
| 152 | contact guard, feedthrough pin | 153 | slot, contact guard |
| 154 | middle section, contact guard | 155 | mid-section, contact |
| 156 | edge, contact | 157 | edge, contact guard |
| 158 | cutout, contact guard | 159 | tine, receptacle contact |
| 160 | inflection form, receptacle contact | 161 | mid-section wall |
| 170 | receptacle contact | 171 | weld line |
| 181 | preload, internal | 191 | receptacle contact |
| 192 | contact guard | 193 | head, feedthrough pin |
| 194 | feedthrough pin | 195 | base, contact guard |
| 196 | weld line | 201 | mid-section, contact |
| 202 | slot edges, contact guard | 203 | inflection point, contact |
| 204 | cutout, contact guard | 205 | preload, contact guard |
| 210 | receptacle contact | 211 | contact guard |
| 212 | mating end, contact | 213 | tip, contact guard |
| 214 | contact guard arm | 220 | preload location |
| 221 | weld line | 222 | weld line |
| 230 | receptacle contact | 231 | contact guard |
| 232 | end, contact tine | 233 | base, contact guard |
| 234 | weld line | 235 | weld line |
| 236 | preload area | 240 | receptacle contact |
| 241 | contact guard | 242 | weld line |
| 243 | weld line | 244 | arm, contact guard |

DETAILED DESCRIPTION

FIGS. 1-10

Connector with Stamped Contact Guard

Figure 1B:
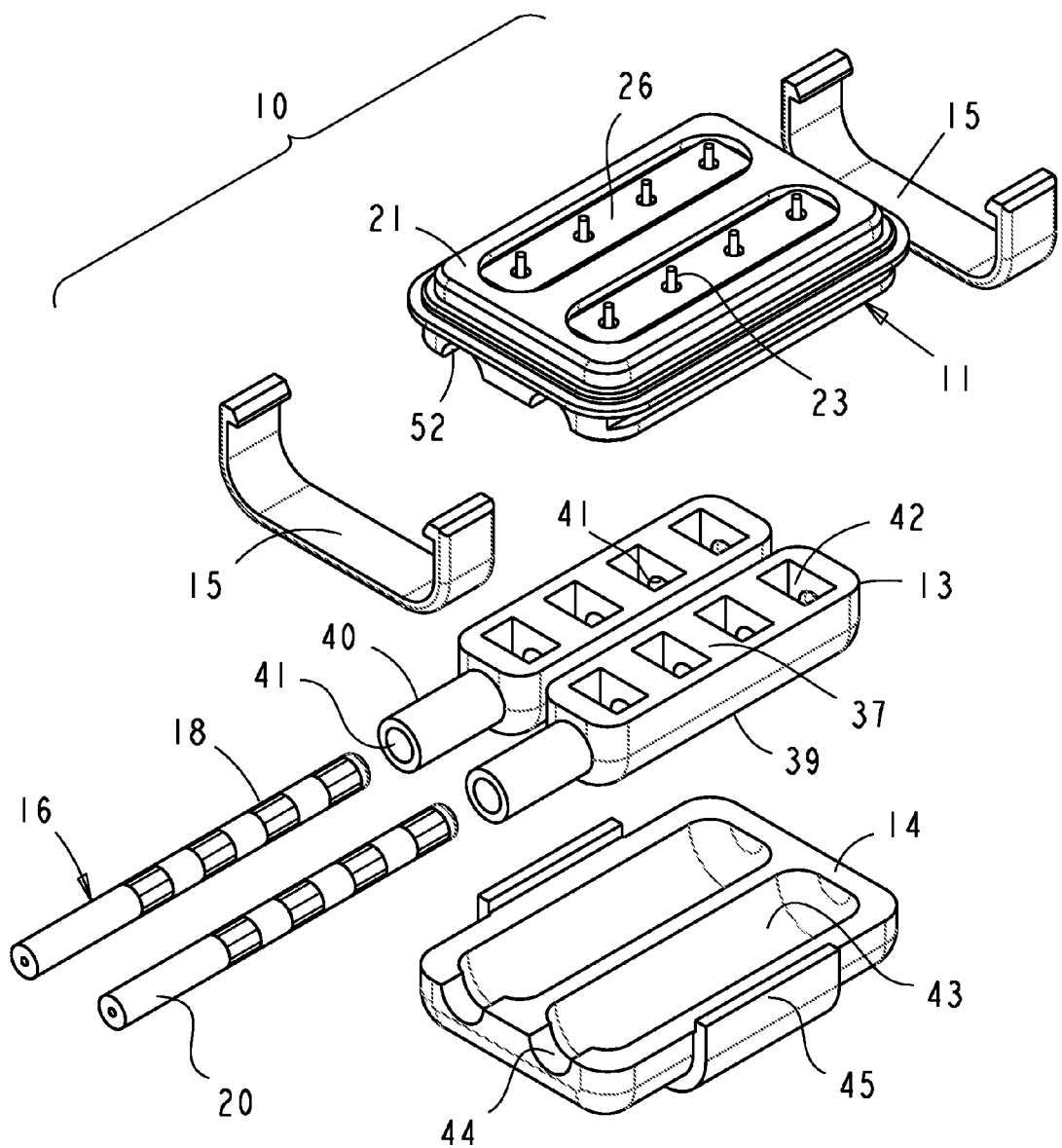

FIGS. 1A and 1B are exploded perspective views, top and bottom views respectively, of an implantable connector 10 which comprises a hermetic feedthrough 11, receptacle contact assemblies 12, seals 13, and a clamping means comprising a clamping cover 14 and retention clips 15.

Figure 1C:
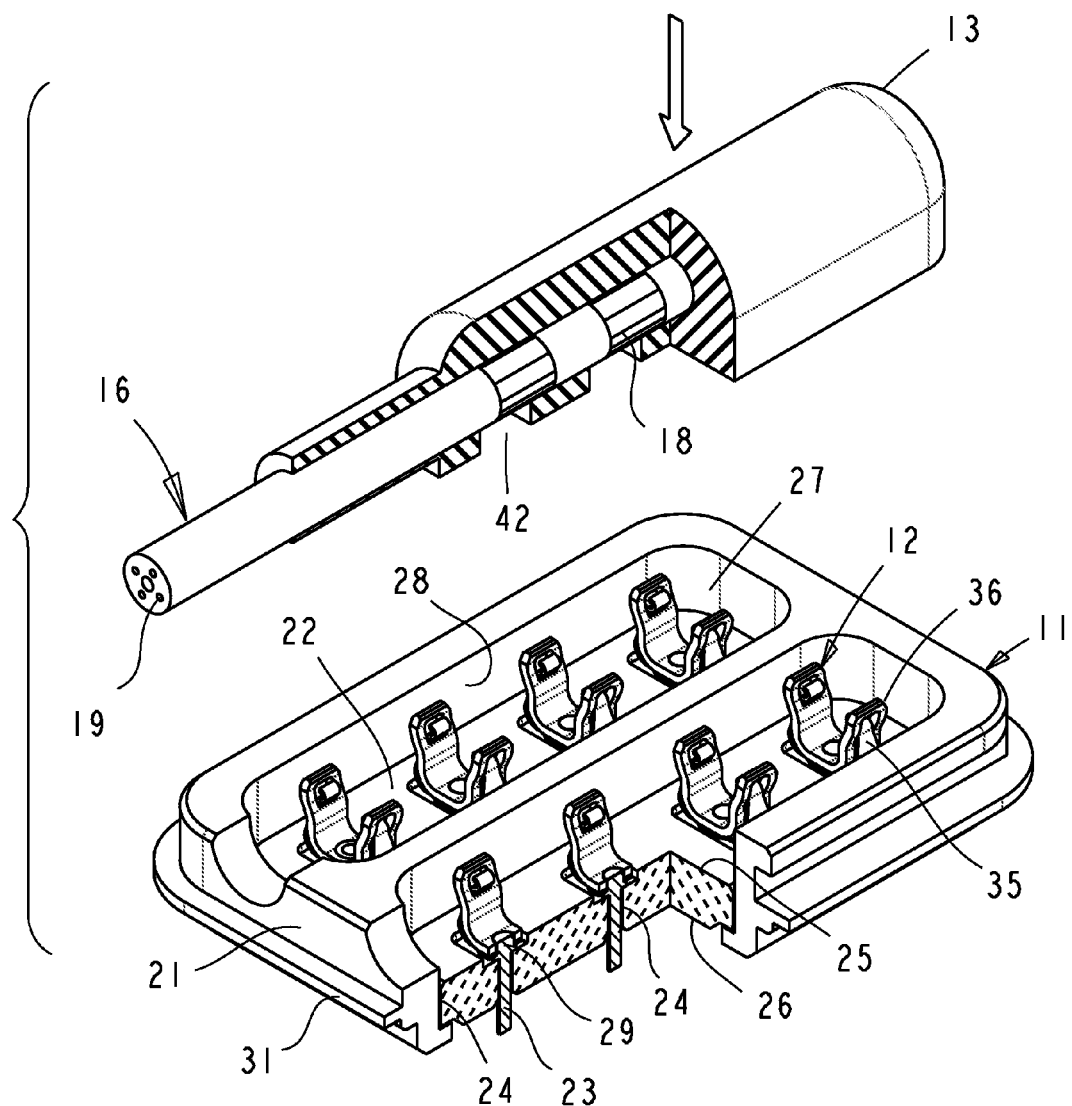
FIG. 1C is a partially cross-sectioned perspective view of the feedthrough assembly of FIG. 1A with a lead-seal assembly positioned for mating.

Connector 10 provides a mating interface for two leads 16. Only lead ends proximal to the connector are shown. Each lead proximal end 17 has plurality of lead contacts 18, which typically have a tubular or ring form. The lead contacts are joined and electrically connected to respective conductors 19 of the lead (FIG. 1C). The conductors are confined within an insulating lead body 20 and connect to the respective sensing and/or stimulating electrodes at the lead's distal end. The lead's distal end, containing the electrodes, is implanted in body tissue targeted for sensing and/or stimulation (not shown; the method of such implantation is well known in the medical field and is not relevant here).

Turning to FIG. 1C where the discussed components are shown in a larger scale, feedthrough 11 comprises a housing 21, at least one dielectric substrate 22, and a plurality of feedthrough pins 23. These components are assembled as shown but without receptacle contact assemblies, and are joined together using a biocompatible braze 24. Resilient contacts are preferably added to a finished feedthrough, i.e., after brazing, in order to avoid degradation of contact spring properties due to high brazing temperature. Dielectric substrate 22 has exterior or connector side 25, and interior or device side 26 (better seen in FIG. 1B). Feedthrough pins 23 are hermetically sealed in the dielectric substrate to provide pass-through connections from the exterior side to the interior side of the substrate.

The feedthrough has at least one exterior cavity 27, formed by the exterior side of the dielectric substrate and inside walls 28 of the feedthrough housing, where the connector is assembled. Each feedthrough pin has an external end or head 29, communicating with the feedthrough exterior cavity. The feedthrough becomes an integral part of an implantable device's hermetic envelope once the feedthrough is joined to the device's hermetic case 30 (FIG. 2) along welding flange 31 of the feedthrough housing.

The medical feedthrough materials and assembly techniques are well known in the art and are discussed in more detail in published US Patent Application 2007/0134985 A1 to Frysz et al. Currently preferred but non-limiting examples of materials include titanium or titanium alloys for the housing, highly purified aluminum oxide (pure alumina ceramic) for the dielectric substrate, platinum and platinum-iridium alloys for the feedthrough pins, and pure gold for brazing.

Receptacle contact assembly 12 comprises receptacle contact 35 and contact guard 36. The receptacle contact assembly is attached to the top perimeter of head 29 of the feedthrough pin. Circular head profile is shown, but non-circular profiles (e.g., oblong or rectangular) can also be employed. Each receptacle contact 35 is electrically connected to respective feedthrough pin 22, and designed to slidably engage with a corresponding contact 18 of the lead.

Returning to FIGS. 1A and 1B, each seal 13 has a substantially flat bottom 37 (FIG. 1B) cooperating with the exterior side of the dielectric substrate, a side perimeter 38 cooperating with the inside walls of the feedthrough housing, a profiled top 39, a sleeve 40, and a circular lumen 41 for receiving the proximal end of the lead. The seal further has apertures 42 (FIG. 1B) communicating with lumen 41.

Clamping cover 14 has at least one pocket 43, cooperating with profiled top 39 of the seal, and a corresponding channel 44 cooperating with sleeve 40 of the seal. The cover further has extended side walls 45 to facilitate alignment of the cover to the feedthrough during connector assembly.

The seal can be molded from a medical silicone polymer or other medical grade elastomer that provides sealing features when compressed. Seal surfaces and cooperating surfaces of other components may incorporate a low-friction polymeric lining or coating, such as a poly-para-xylylene (sold under the trademark Parylene by Specialty Coating Systems, Indianapolis, Ind.), to reduce sliding friction and to assure easy separability of components after prolonged use under pressure. The retention clip can be stamped or machined from a biocompatible high strength alloy, such as titanium alloy 6A1-4V. The clamping cover can be fabricated from a biocompatible material such as titanium, titanium alloy, or a hard polymer such as polyetheretherketone (PEEK), preferably reinforced (e.g., filled with carbon fibers) to increase strength and stiffness Implantable-grade PEEK, also known as PEEK-OPTIMA is available from Invibio, Inc. Ceramic materials such as pure alumina or toughened alumina are also suitable clamping cover materials.

In order to mate the lead to connector 10, lead proximal end 17 is first inserted into a circular lumen 41 of seal 13, as shown in FIG. 1C, without significant interference (preferably less than 1Newton axial insertion force). Once the lead proximal end is protected by the seal, the lead-seal assembly is inserted into feedthrough cavity 27, preferably with slight interference. The slight interference fit is advantageous since it assures secure holding of the lead-seal assembly in the feedthrough cavity through the final steps of connector assembly. The seal cooperates with the feedthrough cavity to align lead contacts 18 with corresponding receptacle contacts 35 and to provide contact electrical isolation sealing when the connector is clamped. The receptacle contacts access the lead contacts via apertures 42 in the seal.

Figure 2:
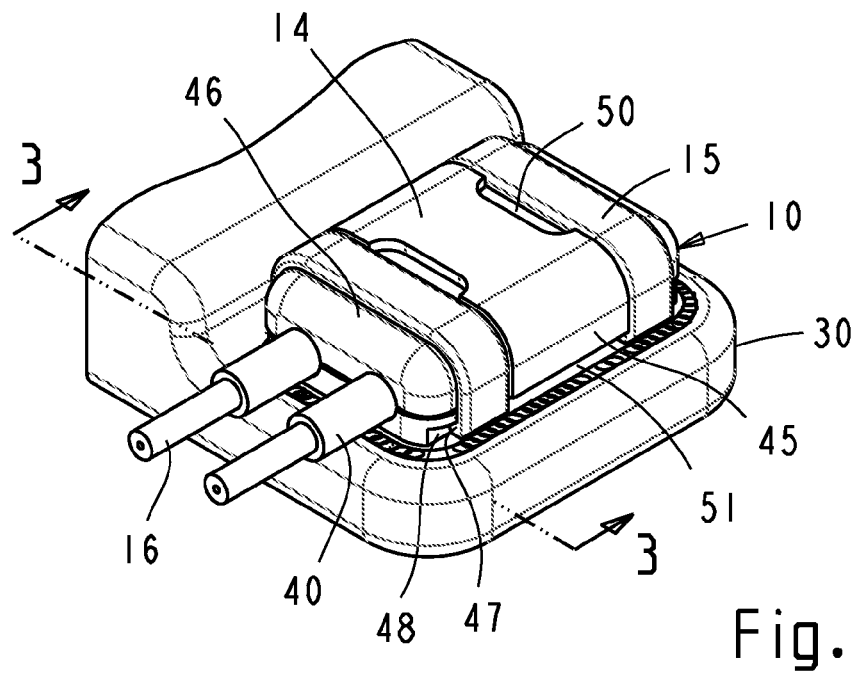
FIG. 2 is a perspective view of the fully assembled (mated and clamped) connector of FIG. 1A.

FIG. 2 is a perspective view of a fully assembled connector 10. The lead-connector assembly is maintained in a mated condition by clamping cover 14 which is secured to the feedthrough housing with retention clips 15. The clips can be installed from the top or inserted from the sides after the cover is pressed against seal 13. Detent features, such as a slight protrusion on the cover in front of the clip, e.g., in location 46, can be used to seat the clip securely and to prevent unintended dislodging of the clip in a sideways or lateral direction after assembly. Retention clip latches 47 engage undercuts 48 on the side walls of feedthrough housing 21 to maintain the connector in a mated state. Relief cuts 50 on the top of clamping cover 14 enable the clips to be removed by inserting a flat blade screwdriver or other surgical tool in such cuts.

If desired, a simple clamping tool (not shown) can be used to temporarily clamp the connector in order to facilitate installation and/or removal of the clips. Feedthrough undercuts 48 extend along the length of the feedthrough's sides so that the temporary clamping tool with pivoting side latches and a clamp can engage the undercuts at side mid-points 51 and force the cover down with a quick action screw or cam. The tool is removed after disengaging the tool's latches by pivoting them away from the feedthrough's undercuts.

Clamping of the connector completes the slidable engagement of the lead contacts with the corresponding receptacle contacts. The receptacle contacts electrically connect lead contacts 18 to the corresponding feedthrough pins. Concurrent with contact engagement, seals 13 are compressed by the clamping cover against exterior side 25 of dielectric substrate 22 to seal (isolate) the adjacent seal apertures along the exterior side of the dielectric substrate (interfacial seal) and between lead contacts 18 along seal lumen 41. The side perimeter 38 of the seal is pressed against inside walls 28 of feedthrough cavity to provide a peripheral seal. In order to assure uniform distribution of the seal pressure, cover pocket 43 conforms to top 39 of the seal. Cover channel 44 and a similar channel 52 in the feedthrough housing are designed to radially compress seal sleeve 40 in order to seal lead body 20 at the exit from the connector. The cover has extended side walls 45 to aid in alignment of the cover to the feedthrough. Seal sleeve 40 extends beyond connector to provide protection and strain relief for the exiting lead.

The exemplary two-lead connector shown in FIG. 2 can be less than 6.0 mm thick, 11.0 mm wide, and 15.0 mm long.

Figure 3:
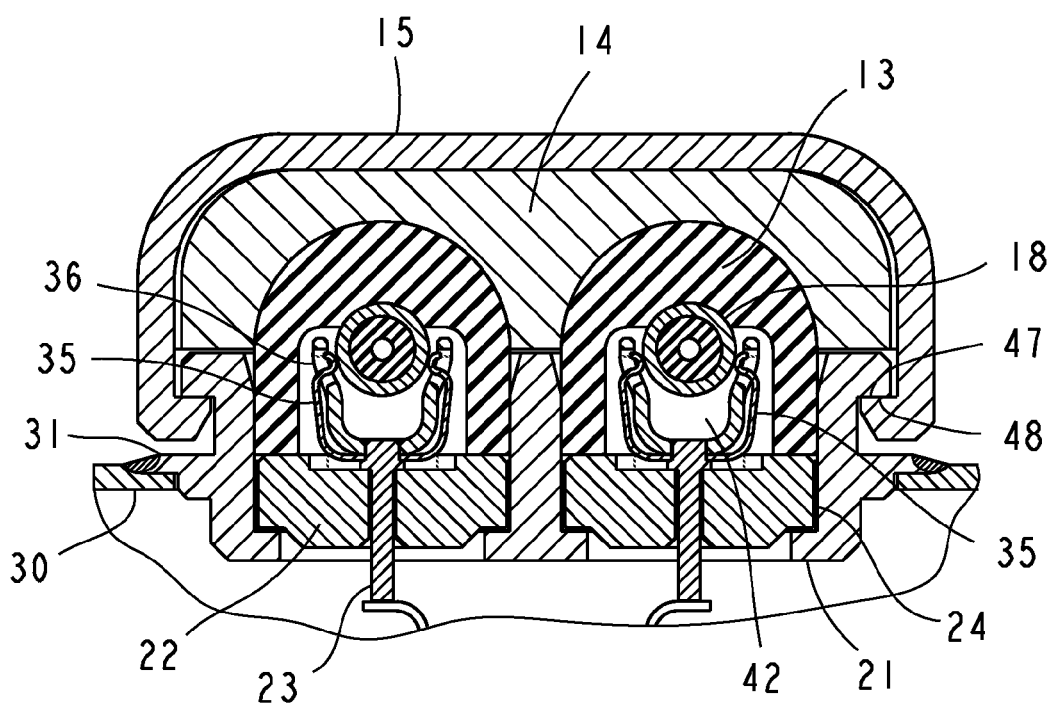
FIG. 3 is a cross-sectional view of the connector of FIG. 2, taken through the contacts, in the plane normal to the leads, as indicated by the line 3-3 of FIG. 2.

FIG. 3 is a cross-sectional view of the mated connector of FIG. 2 taken through the contacts in the plane normal to the leads, showing internal details of the connector mating interface. Each lead contact 18 is engaged with corresponding receptacle contact 35, thus making connection to the device's electronics via hermetic feedthrough pins which extend into the interior of the device's case 30. The seal isolates electrical connections contained within each seal aperture 42. The electrically non-common connections are thus sealed from each other and from other conductive components such as feedthrough housing 21, and are protected from ingression of body fluids, which also tend to be conductive.

Figure 4:
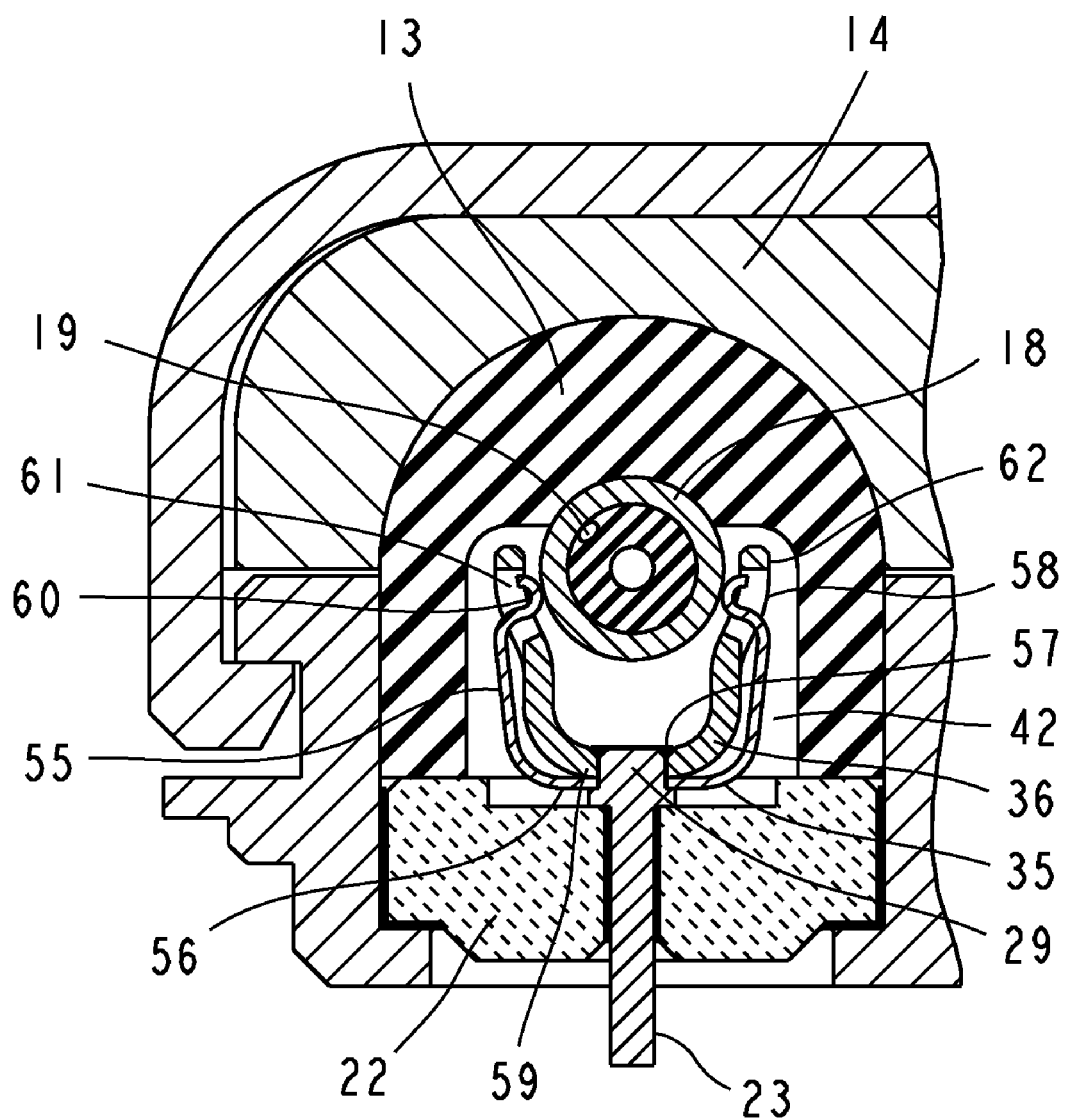
FIG. 4 is an enlarged, partial view of FIG. 3.

FIG. 4 is an enlarged partial view of the connector of FIG. 3 which shows more clearly the contact system. Contact assembly is located on head 29 of feedthrough pin 23, and is welded to the head's top perimeter at 57. Head 29 of the feedthrough pin and hole 53 (FIG. 5) in the contact guard have complementary profiles to facilitate alignment and attachment along corresponding edges at 57.

Each lead contact 18 is engaged with the corresponding receptacle contact 35 in a separate aperture 42 of the seal. The receptacle contact has resilient tines or springs 55 which extend from the contact's mid-section 56. The contact tines may have a tapered width (FIG. 5) to optimize contact spring parameters. The contact tines are protectively shielded by contact guard 36. The contact guard has side arms 58 extending from middle section or base 59. Only mating ends 60 of the contact tines extend into the lead contact mating area via cutouts 61 in the contact guard arms 58. The contact guard arms have tips 62 which extend beyond the contact mating ends 60 to prevent an unintended access to the contact tines.

Figure 5:
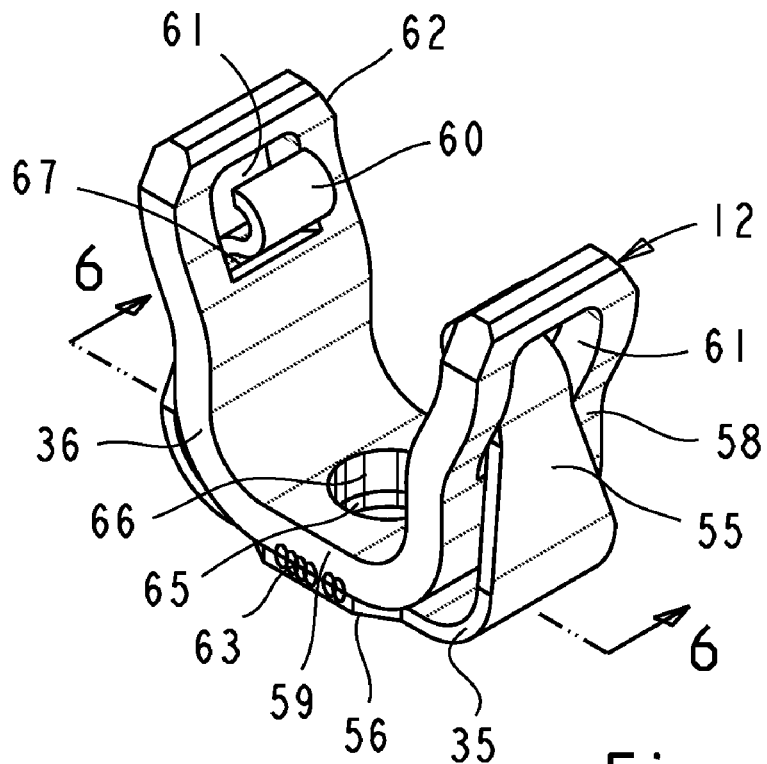
FIG. 5 is a perspective view of the contact assembly of FIGS. 1-4 showing the U-shaped receptacle contact joined to the contact guard.
Figure 6:
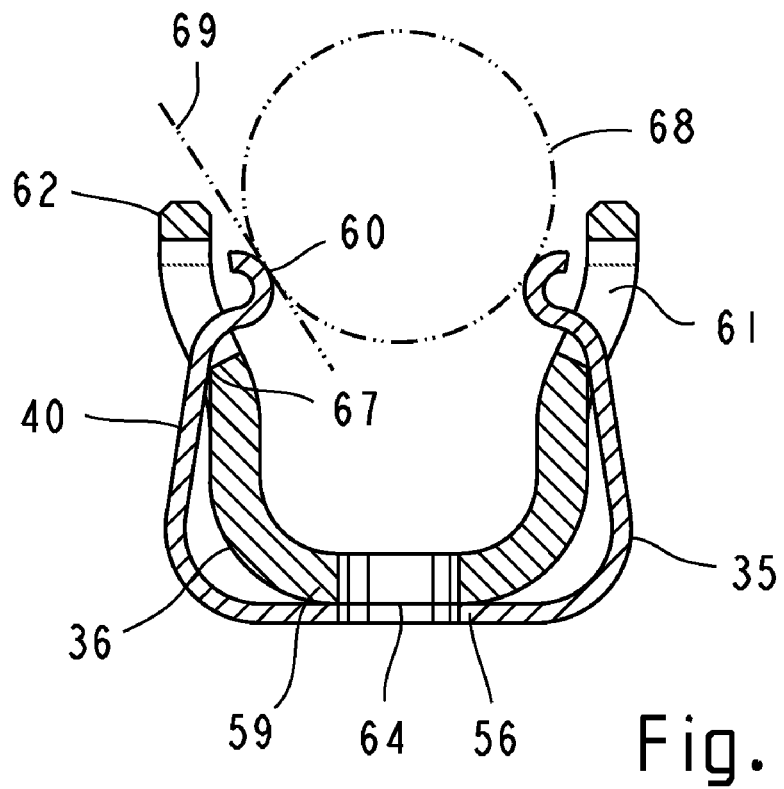
FIG. 6 is a cross-sectional view of the contact assembly taken as indicated by the line 6-6 of FIG. 5.

FIGS. 5 and 6 show contact assembly 12. Receptacle contact 35 and contact guard 36 are joined together edge-to-edge along corresponding edges of contact mid-section 56 and contact guard base 59. The resulting weld line is shown at 63. Alternatively, the receptacle contact's mid-section can be joined to the underside surface of base 59 around mid-point 64 (FIG. 6). Holes 65 (in the contact's mid-section) and 66 (in the contact guard's base) can be used to align the parts together and, during assembly in the feedthrough, to locate the contact assembly on the feedthrough pin head for joining to the feedthrough pin. In thus joined condition, the mating ends of the receptacle contact tines pass through cutouts 61 and are protected therein from unintended access. Each contact tine is preloaded against corresponding edge 67 in cutout 61. The contact preload assures consistent contact force and desirable engagement characteristics. Since the contact gap in the preloaded contact is larger than in the contact's free-state (as stamped), the initial engagement occurs at a more favorable angle. An outline of the lead contact at the beginning of engagement is indicated by circle 68. The initial engagement angle is indicated by tangency line 69. The final contact engagement points can be where the lead contact is the widest or, for a circular lead contact, at the lead contact's center plane. Alternatively, the contact points can be slightly below the center plane or even significantly below the lead contact's center plane if desired.

The contact guard protects the receptacle contact from damage by shielding the contact and limiting the contact tine excursion due to unintended contact (e.g., by a human hand, a surgical tool, or a mismated component). Excessive movement of contact tines toward each other (closing contact gap) is prevented by support at preload edges 67 and an unintended outward movement (opening contact gap) is prevented by shielding the contact mating ends by tips 62 of the contact guard arms. The tips extend beyond the contact's mating ends thus shielding the mating ends from unintended touching from above. Contact guard structure is substantially more rigid than the receptacle contact and thus less susceptible to accidental damage.

The receptacle contact can be formed from a high-strength biocompatible alloy, such as 80Pt-20Ir platinum-iridium alloy, which can be drawn into a high-strength fine ribbon or strip with a good formability. The contact guard can be formed from platinum, platinum-iridium alloy, or other biocompatible alloy with affinity for welding to the receptacle contact and to the feedthrough pin. The receptacle contact's material thicknesses can be less than 0.08 mm while the thickness of the contact guard material can be 0.20 mm or greater.

FIGS. 7-10

Other Contact Assembly Variations with Stamped Contact Guard

Figure 7:
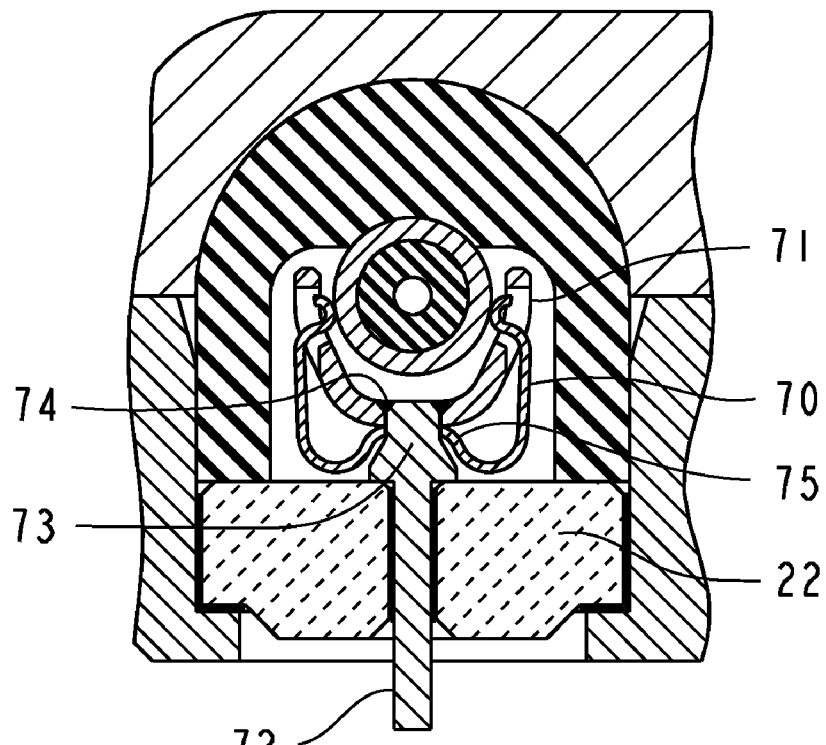
FIG. 7 is a partial cross-sectional view of a fully assembled connector (a variation of FIG. 4) with a W-shaped receptacle contact.

FIG. 7 is a partial cross-sectional view of a fully assembled connector similar to that in FIG. 4. Receptacle contact 70, contact guard 71, and feedthrough pin 72 are variations of the corresponding components in connector 10. Receptacle contact 70 has an inflection form at mid-section 75 to provide a longer spring in the available space. (The contact is W-shaped and thus can have a longer spring length than a U-shaped contact of comparable height.)

Figure 8:
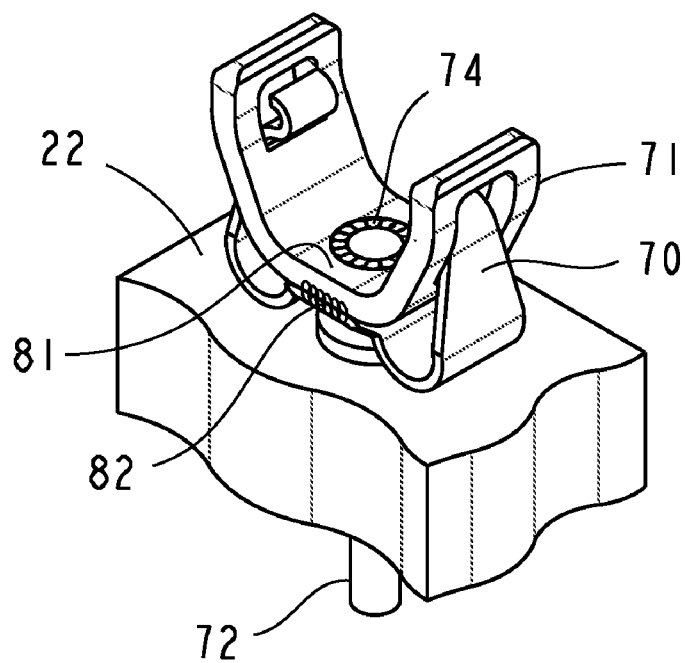
FIG. 8 is a perspective view of the W-shaped contact assembly of FIG. 7.

FIG. 8 is an isometric view of the contact assembly of FIG. 7, attached to feedthrough pin 72 and shown with a segment of dielectric substrate 22. As in contact assembly 12, mid-section 75 of the receptacle contact is joined to base 81 of the contact guard along corresponding outside edges at 82 on both sides of contact assembly (one side shown in FIG. 8). The thus obtained contact assembly is located on a head 73 of feedthrough pin 72 and is welded to the feedthrough pin's head top perimeter at 74.

Figure 9:
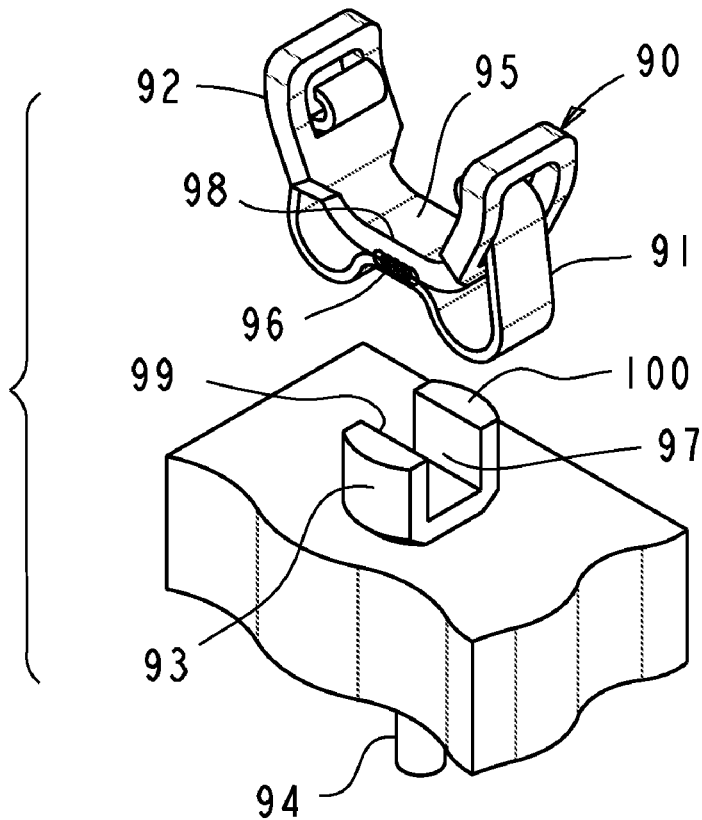
FIGS. 9 and 10 are a variation of a W-shaped contact assembly of FIG. 8, adapted for attachment to a slotted head of the feedthrough pin.
Figure 10:
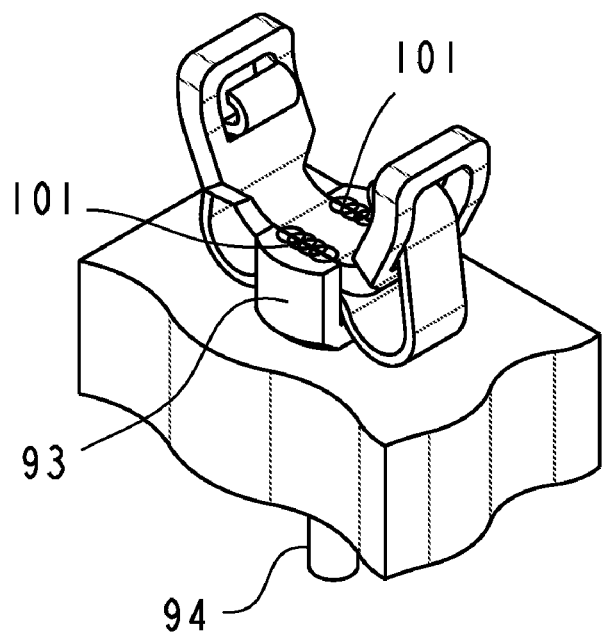

FIGS. 9 and 10 show an alternative contact assembly 90 comprising a W-shaped receptacle contact 91 and a contact guard 92, adapted for attachment to a slotted head 93 of a feedthrough pin 94. The receptacle contact has substantially uniform width and can be formed from a flat wire or ribbon stock. The width of the contact guard at base 95 is matched to the receptacle contact's width so that the contact can be attached to the contact guard, edge-to-edge, along corresponding mid-section edges at 96 (on both sides of the assembly), preferably by welding. Alternatively, the mid-section of the receptacle contact can be attached to the underside surface of the contact guard's base. The feedthrough pin head has a slot 97 sized to accommodate the contact guard's base 95 with a close fit. The contact assembly is attached to a feedthrough pin by inserting the contact assembly into slot 97 until the top surface of contact guard's mid-section 95 is co-planar with top surface 100 of the feedthrough pin head and joining edges 98 of the contact guard with the corresponding edges 99 of the feedthrough pin head, preferably by welding. The resulting weld lines 101 are shown in FIG. 10.

FIGS. 11-14

Contact Assemblies with Machined Contact Guard

Figure 11:
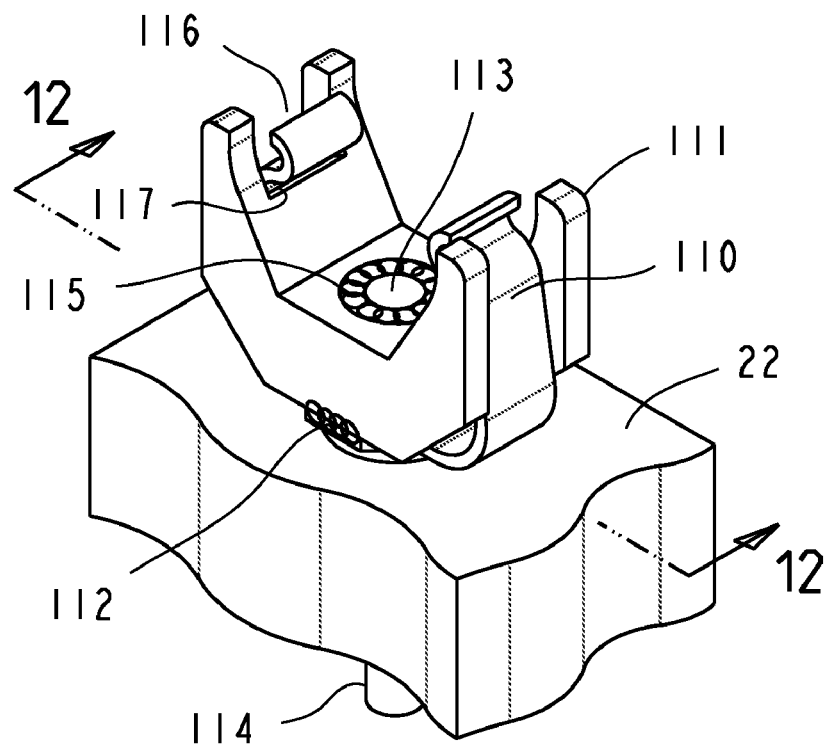
FIGS. 11 and 12 are a variation of a contact assembly with a U-shaped receptacle contact and a contact guard suitable for machining.
Figure 12:
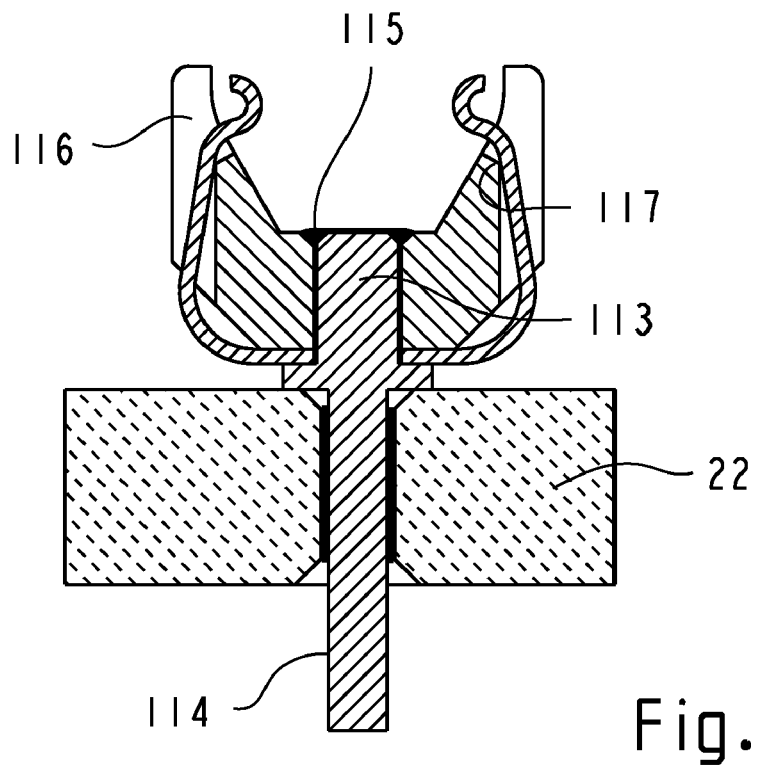

FIGS. 11 and 12 show a variation of the contact assembly comprising a U-shaped receptacle contact 110 with contact guard 111. This contact assembly is similar to contact assembly 50, except the contact guard is adapted for machining and can be made more rigid than a stamped counterpart. The receptacle contact and the contact guard are joined together at 112 on both sides of the assembly. The contact assembly is attached to the top of a head 113 of a feedthrough pin 114 by a weld line 115. The receptacle contact tines are protectively shielded in slotted sides 116 of the contact guard arms and are preloaded at 117.

Figure 13:
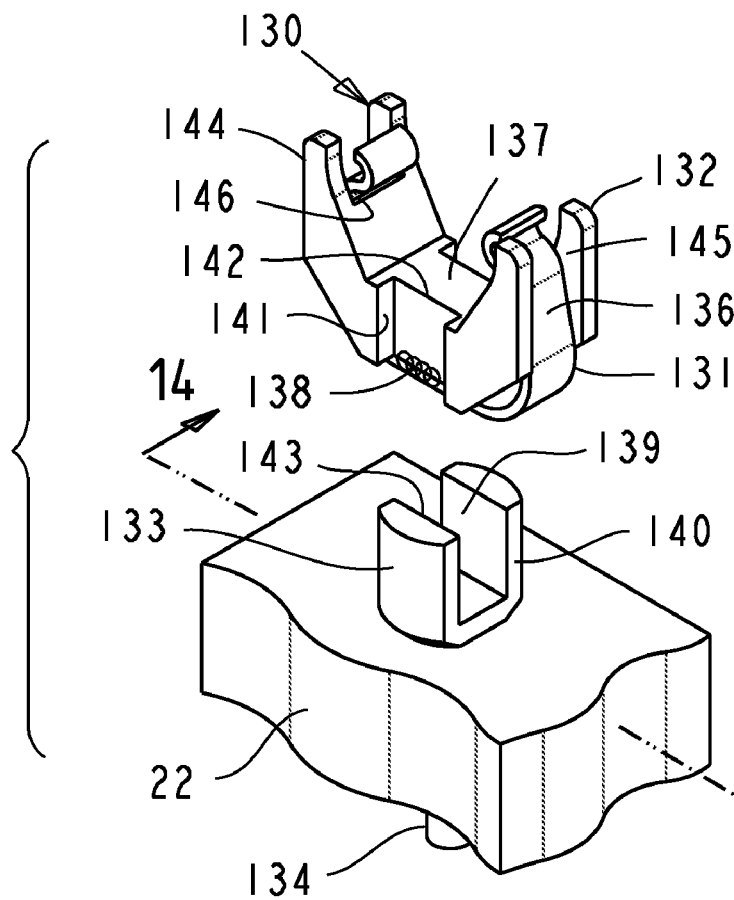
FIGS. 13 and 14 are a variation of a contact assembly with a U-shaped receptacle contact and a machined contact guard, interfaced to a slotted head of the feedthrough pin.
Figure 14:
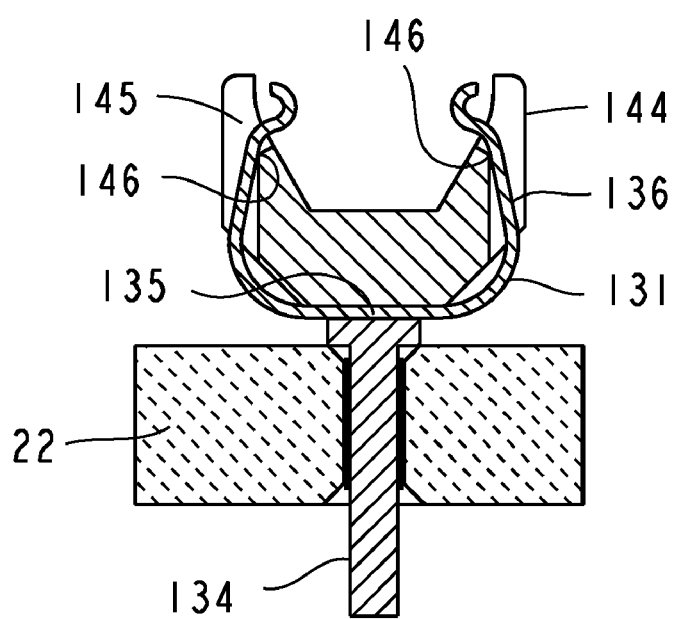

FIGS. 13 and 14 show an alternative contact assembly 130 with a U-shaped receptacle contact 131 and a machined contact guard 132, designed to attach to a slotted head 133 of a feedthrough pin 134. The receptacle contact's mid-section 135 and resilient tines 136 have substantially the same width and can be formed from a flat wire or ribbon stock. The width of the contact guard at base 137 is matched to the contact's width so that the contact can be attached to the contact guard's base, edge-to-edge, along the corresponding outside edges at 138, preferably by welding. Alternatively, the mid-section of the receptacle contact can be attached to the underside of the contact guard's base by edge-to-surface or surface-to-surface welding.

The feedthrough pin head has a slot 139 and a flat face 140 at each end of the slot, the flat faces defining the slot's length. Slot 139 is sized to receive the base of the contact guard and the slot length is sized to fit between steps 141 in the base. The stepped width of the contact guard's base enables contact assembly 130 to self-align to the pin's head for joining. When the contact assembly is nested in slot 139, the relative lateral movement and rotation of the components is prevented, eliminating the need for special locating fixtures. The corresponding edges 142 (in the contact guard) and 143 (in the feedthrough pin) are joined together by welding. The contact guard's side arms 144 have slots 145 sized to accommodate the resilient contact tines with a small operating clearance (to allow unimpeded contact deflection). Contact tines 136 are protectively shielded in the slotted arms of the contact guard and can be preloaded against the contact guard at 146.

FIGS. 15-18

Contact Guard Integral with Feedthrough Pin

Figure 15:
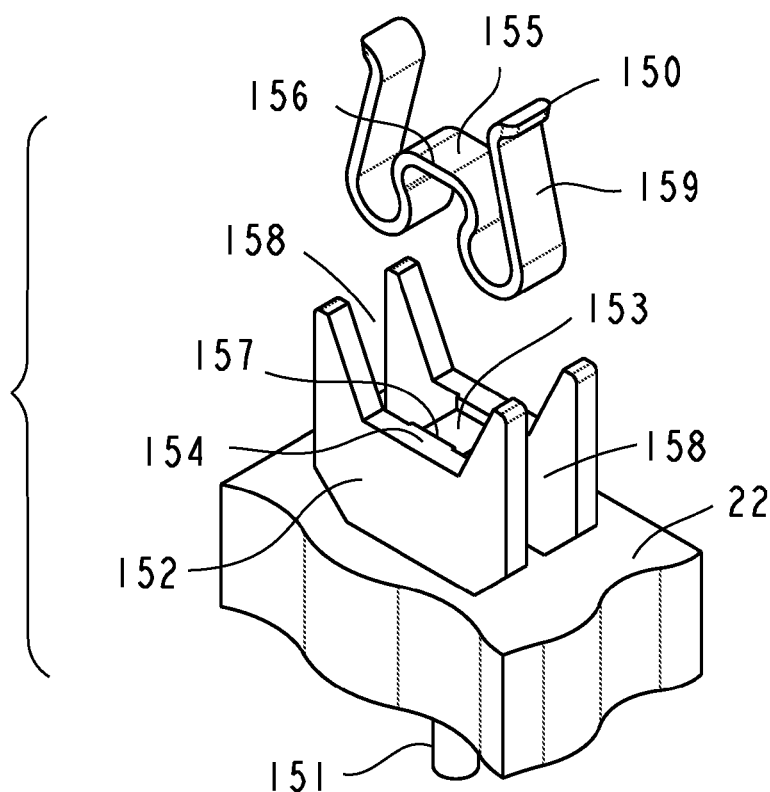
FIG. 15 is a contact assembly variation with a W-shaped contact that attaches directly to the feedthrough pin with an integral contact guard.

FIG. 15 shows details of a contact system with a W-shaped contact 150 that attaches directly to a feedthrough pin 151 with integral contact guard 152. The receptacle contact has substantially uniform width and can be formed from a flat wire or ribbon stock. The contact guard has a shallow slot 153 on the top of middle section 154. The depth of the slot is approximately equal to the contact material's thickness and the width of the slot is sized for a close fit with the contact's mid-section 155. After locating in slot 153, the receptacle contact is attached to the contact guard of the feedthrough pin by welding along corresponding edges 156 (in the contact) and 157 (in the contact guard). Alternatively, slot 153 may be omitted and the receptacle contact can be attached directly to the top surface of the contact guard's mid-section 154.

The contact guard has cutouts 158 to form slotted sides which protectively confine the contact tines 159. Cutouts 158 are slightly wider than the contact tines width to allow unimpeded movement of the contact tines during connector mating. Slot 153 is slightly narrower than side cutouts 158 to assure precise positioning for welding and to enable centering (equal clearance on both sides) of the tines in the side slots. The inflection form 160 can be made for close fit with the sides of contact guard's mid-section wall 161 to facilitate a self-alignment of the receptacle contact to the contact guard for welding.

Figure 16:
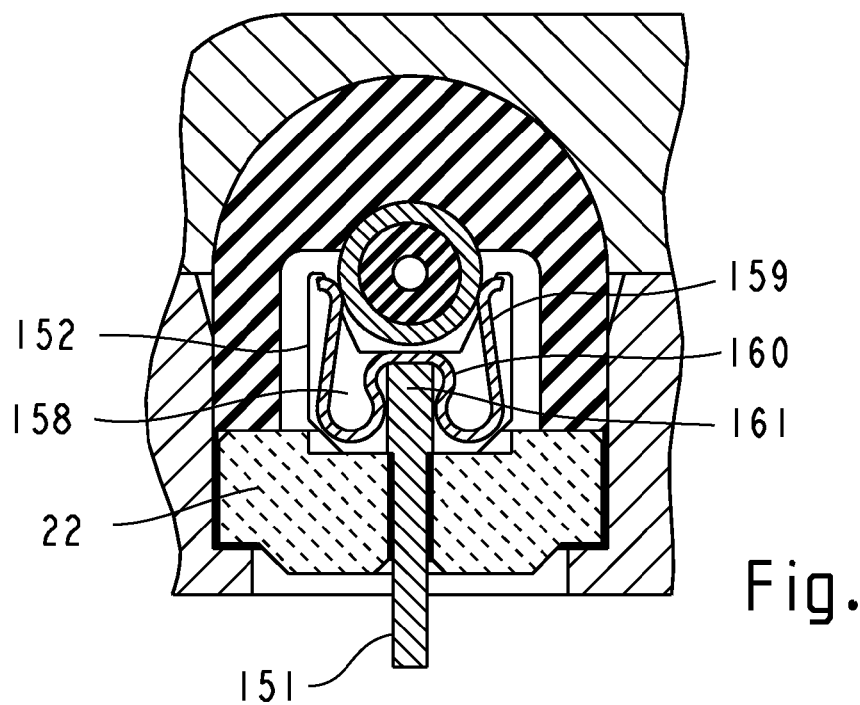
FIG. 16 is a partial cross-sectional view of a fully mated connector (a variation of FIG. 7) utilizing the contact of FIG. 15.

FIG. 16 is a partial cross-sectional view of a fully assembled connector (equivalent to the cross-sectional views of FIG. 4) utilizing contact 150.

Figure 17:
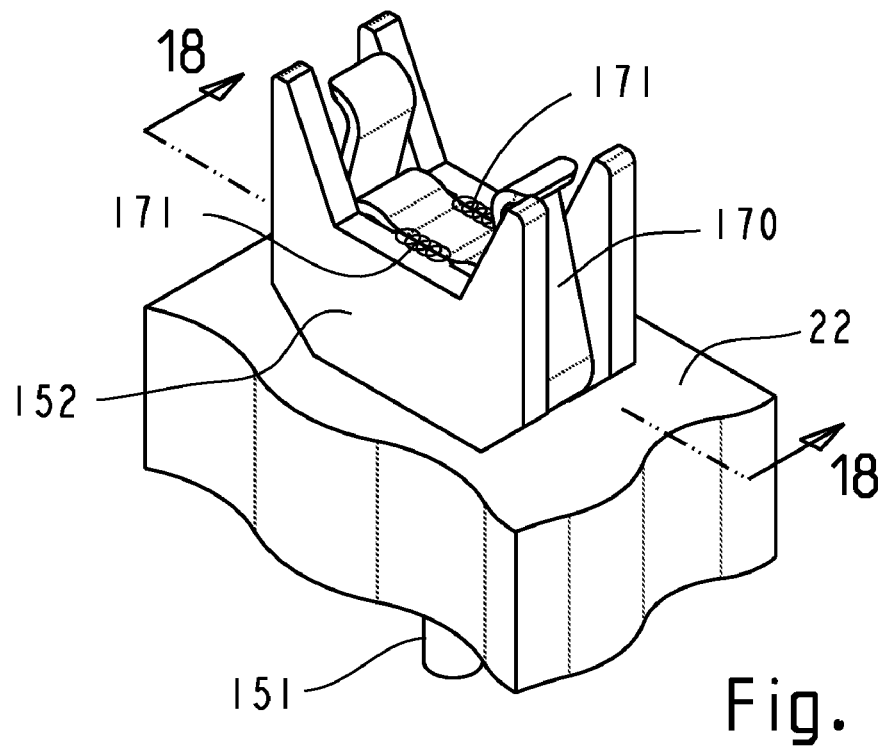
FIGS. 17 and 18 are a variation of the W-shaped contact of FIG. 15 which has a built-in preload.
Figure 18:
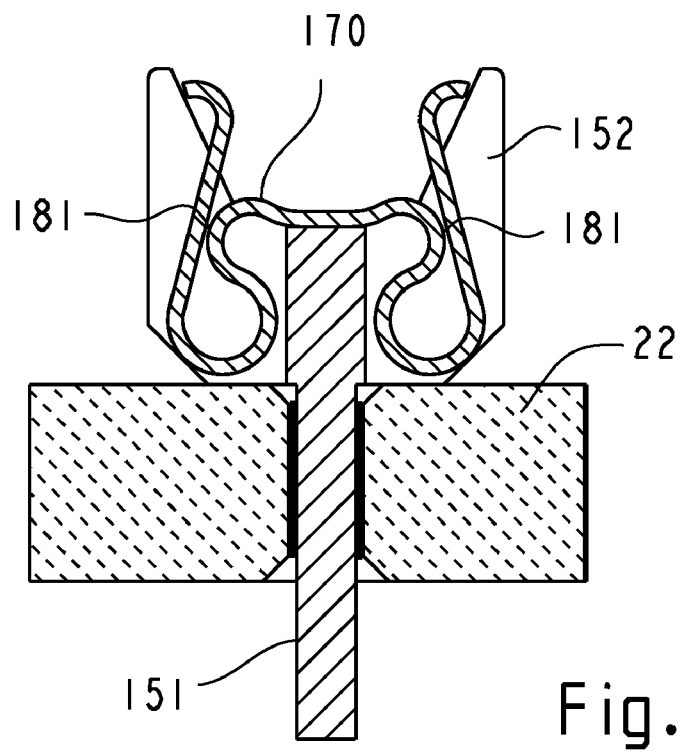

FIGS. 17 and 18 show details of the contact assembly with contact 170, which is a variation of W-shaped contact 150 of FIG. 15. Contact 170 has increased spring length (while occupying the same space as contact 150) and is formed to provide an internal contact preload in the free-state (as formed) condition. The methods of contact joining described in connection with contact 150 are applicable to contact 170. Receptacle contact 170 is attached to contact guard 152 of feedthrough pin 151 at weld lines 171. The internal contact preload is shown at 181.

Figure 19:
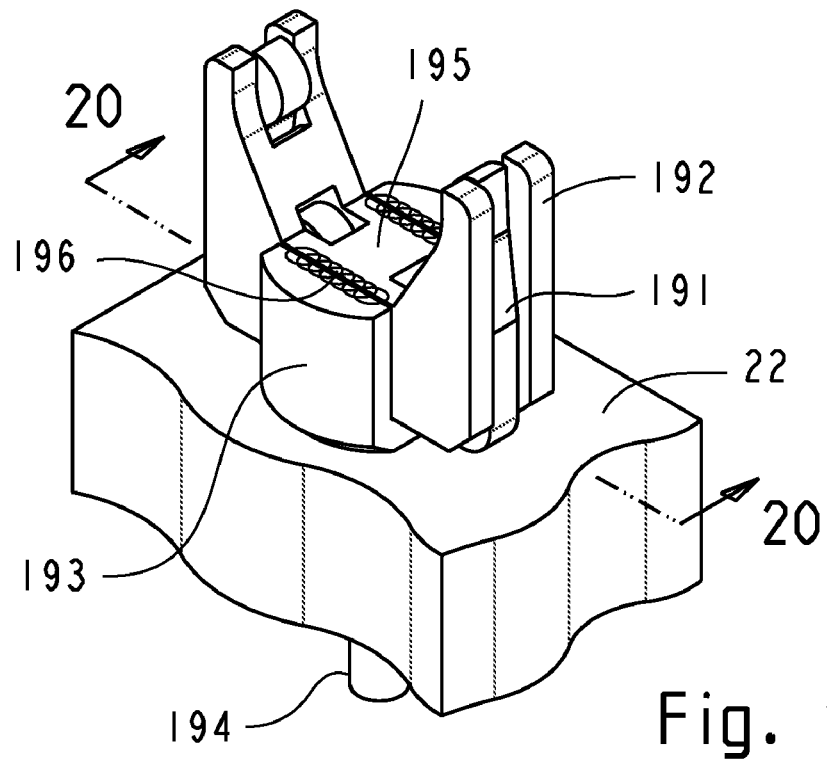
FIGS. 19 and 20 are a variation of contact assembly where a receptacle contact is made as a flat blank, without bending.
Figure 20:
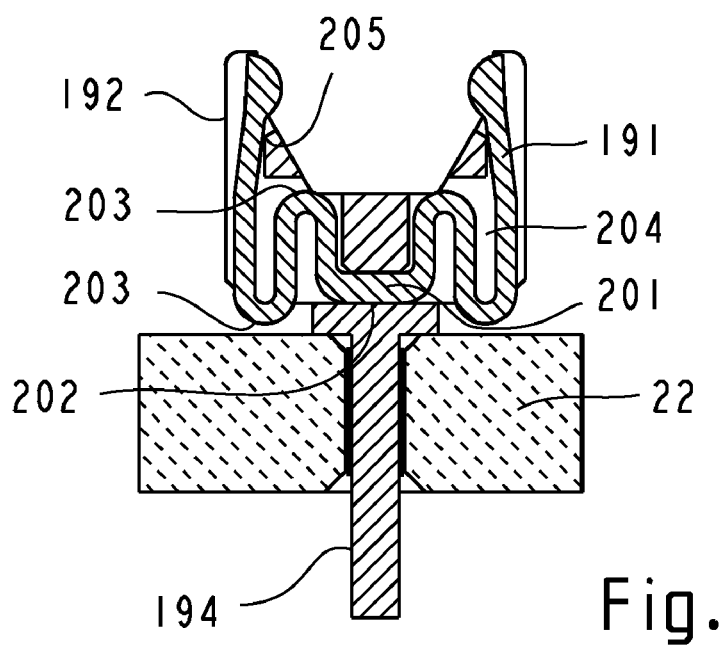

FIGS. 19 and 20

Other Contact Assembly Variations

FIGS. 19 and 20 show a variation of the contact assembly comprising a receptacle contact 191 and a contact guard 192. The contact is designed as a flat blank and can be made by stamping or electrical discharge machining (EDM). The receptacle contact's mid-section 201 is placed in the shallow slot on the underside of the contact guard (FIG. 20) and is attached, preferably by welding, to the contact guard's underside at the slot's outer edges 202. The thus obtained contact assembly is joined to the top of slotted head 193 of feedthrough pin 194 by welding the top edges of the contact guard's mid-section 195 to the corresponding edges of the feedthrough pin head at 196. The contact springs have multiple bends (inflection points) 203 to maximize contact spring length in the available space. The resilient contact tines are protectively confined in cutouts 204, which are slightly wider than the thickness of the contact blank to allow unimpeded contact deflection. The contact tines can be preloaded against contact guard at 205.

Figure 21:
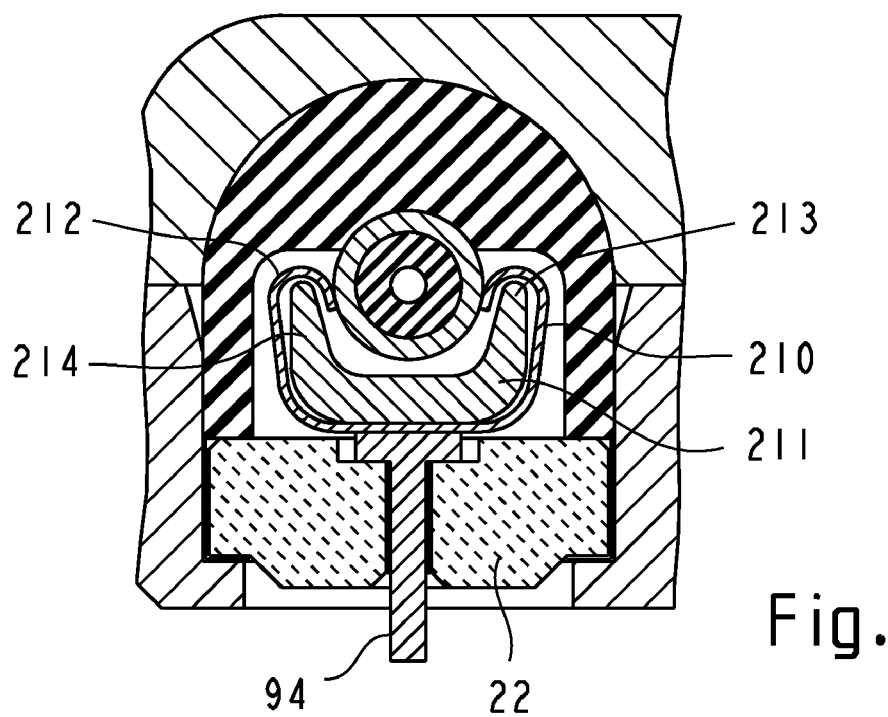
FIG. 21 is a partial cross-sectional view of a fully assembled connector (a variation of FIG. 7) having a U-shaped contact with mating ends wrapping around tips of contact guard arms.
Figure 22:
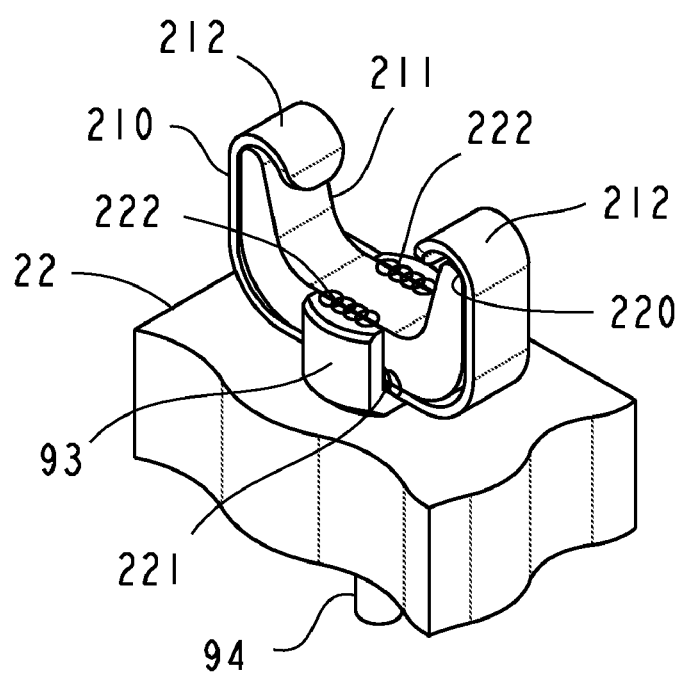
FIG. 22 is a perspective view of the contact assembly of FIG. 21.

FIGS. 21 and 22 show a contact system comprising a U-shaped receptacle contact 210 and a contact guard 211. The partial cross-sectional view of FIG. 21 is similar to that of FIG. 4. The receptacle contact has inwardly formed contact mating ends 212 designed to wrap around tips 213 of contact guard arms 214. The contact's mating ends can be preloaded against outer sides of tips 213 at 220. The receptacle contact and the contact guard have substantially constant and the same widths and are joined together along corresponding outside edges at 221 (only portion of weld line 221 is visible in FIG. 22). The contact assembly is subsequently joined to slotted head 93 of feedthrough pin 94 by weld lines 222. Inwardly formed contact ends 212 cooperate with contact guard tips 213 to limit undesirable excursion of contact ends due to unintended contact, thus preventing contact damage. The allowable contact tine excursion is within the contact's elastic deformation range and therefore does not cause permanent contact deformation.

Figure 23:
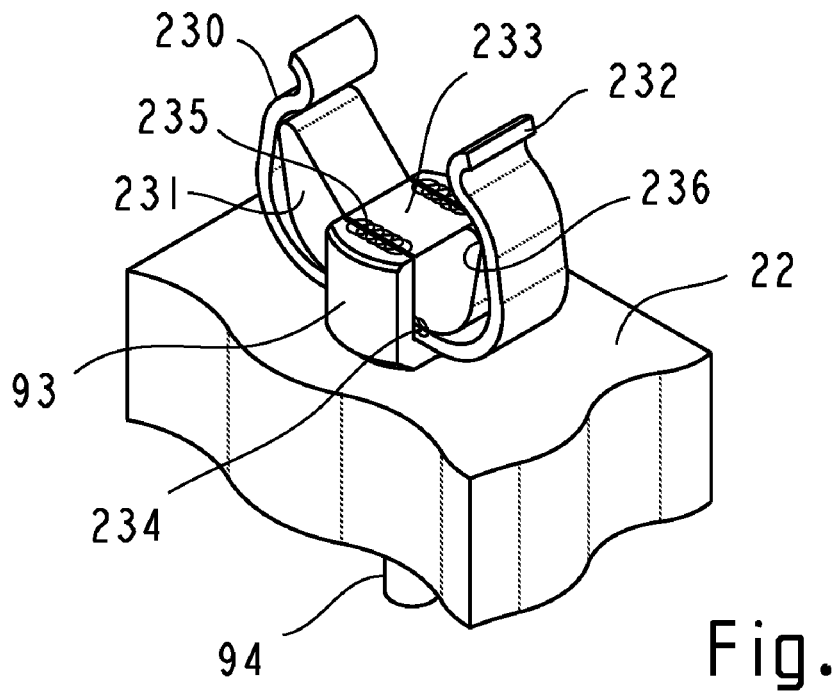
FIG. 23 is a contact assembly variation having a U-shaped contact and a contact guard providing protection from excessive inward deformation.

FIG. 23 is a contact assembly variation with a U-shaped receptacle contact 230 and a contact guard 231. The receptacle contact has outwardly pointing contact tine ends 232. The receptacle contact is welded to the underside of contact guard base 233 along outside edges at 234 (only the beginning of the weld line is visible). The contact assembly is subsequently joined to slotted head 93 of feedthrough pin 94 by weld lines 235. The contact tines can be preloaded against the outer sides of the contact's guard tips at 236. The preload provides desirable contact characteristics and protects contact tines from an inadvertent inward deformation.

Figure 24:
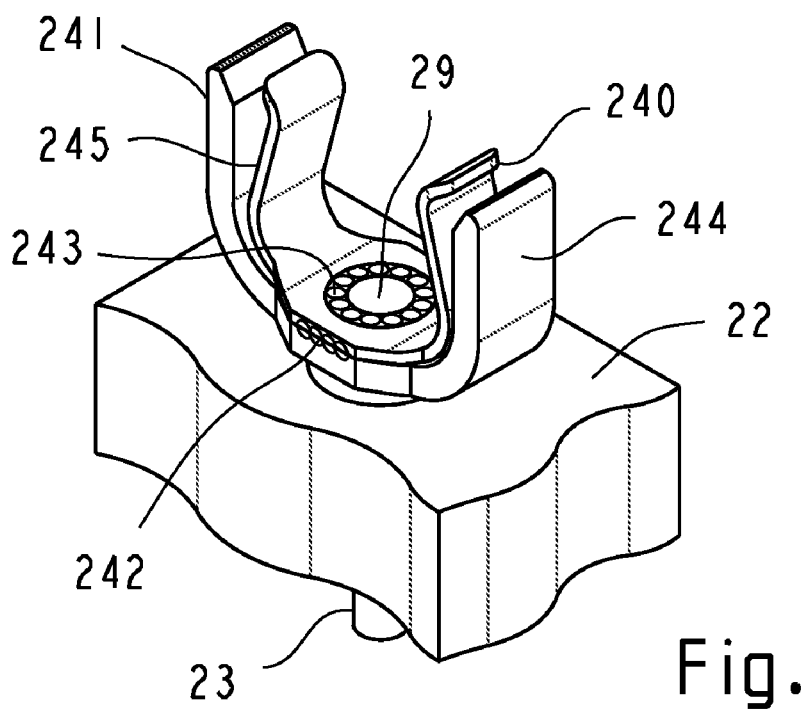
FIG. 24 is a contact assembly variation having a U-shaped contact and a contact guard providing protection against an excessive outward deformation.

FIG. 24 is a variation of a contact assembly with a U-shaped receptacle contact 240 and contact guard 241. The receptacle contact is welded to the contact guard along the contact's midsection outside edges at 242 and the contact assembly is subsequently joined to the round head 29 of feedthrough pin 23 by weld line 243. Contact guard arms 244 shield contact tines 245 from the outside direction and protect the contact tines from an inadvertent outward deformation.

Advantages

From the description above, a number of advantages of various embodiments of the disclosed connector become evident:

(A) A robust contact system is provided which resists damage from unintended contact. The receptacle contact tines are shielded by the contact guard and are thus protected from inadvertent deformation. Allowable contact tine excursion is limited by the contact guard to be within the contact's elastic (recoverable) deflection and therefore does not cause permanent contact damage.

(B) A small contact size is achieved without compromising receptacle contact handling integrity or contact spring parameters. A smaller contact is possible since it is protected by the contact guard. A thinner material can be used to decrease contact size while providing adequate deflection capability, which would be impractical without the protection provided by the contact guard. The free-standing contacts of the prior art are larger (made from the thicker material) to mitigate susceptibility to inadvertent handling damage.

(C) The contact guard can be an integral part of the feedthrough pin or a separate member attached to a feedthrough pin. When attached to the feedthrough pin, the substantially rigid contact guard provides convenient locating features for attachment to a feedthrough pin and enables a robust weld joint.

(D) The contact guard facilitates joining of the receptacle contacts and provides effective protection for the contact-to-guard weld joint. Since an inadvertent contact overloading is prevented by the contact guard, the contact-to-guard joint is not likely to be overstressed. The free-standing contacts of the prior art, which are welded directly to a feedthrough pin, communicate the entire inadvertent contact loading to the contact weld joint, which can thereby be overstressed.

(E) A self-sustaining receptacle contact does not require a clamping force to maintain contact forces, which reduces the structural loading and therefore the size of connector clamping components. The low clamping force enables easy installation and removal of space-efficient clamping hardware without the use of tools. In contrast, when compressible contacts of the prior art are used, a sustained clamping force is required to maintain contact engagement.

(F) The mating tolerances are reduced when a contact with opposing contact tines (preferably preloaded) is used to engage the sides of a lead contact in a sliding manner. The contact's normal forces depend primarily on the receptacle contact gap and the lead contact size. This facilitates consistent contact forces and improved manufacturability.

(G) The sliding contact provides beneficial wiping action to self-clean the contacts at mating (e.g., to displace any tissue debris that may be inadvertently deposited on the contact surfaces).

Further advantages will be evident to those skilled in the art.

Ramifications and Scope

While the connector has been described by means of specific embodiments, numerous modifications and variations known to those skilled in the art or disclosed may be employed without departing from the scope of the invention set forth in the claims. For example, the materials, dimensions, shapes, and sizes of all parts may be adapted to a particular need. The number of contacts in particular can vary greatly (up to 24 or more), thus significantly affecting envelope dimensions of a connector assembly. While a metallic contact guard is preferred because of high strength and stiffness in small size and amenability to welding, the contact guard can be non-metallic (e.g., molded from a medical-grade polymer) and added after the contact is attached directly to a feedthrough pin.

The feedthrough housing may be of two-piece construction, the two pieces joined by welding or another method. The exterior side of the feedthrough housing can be made from a polymer, added after feedthrough brazing operation. The lead contact's cross-sectional profile may be non-circular e.g., rectangular or oblong. When mated, the points of contact can be significantly below the widest section of the lead contact, so that the receptacle contact is at least in part compressive (pushing back on the lead). The contact tines need not be symmetrical and one side of the contact assembly may even be non-resilient. While connector 10 has a separate seal for each lead and a separate feedthrough cavity for each seal-lead assembly, a single seal with two lead-receiving lumens side-by-side can be used so that two leads are accommodated in a single seal which is accommodated in a single feedthrough cavity. A single seal can be replaced with multiple seal components. A seal component can be installed in the feedthrough exterior cavity to serve as a collective contact guard for all receptacle contacts. The seal aperture may be bifurcated (divided by a wall) so that each receptacle contact tine and corresponding contact guard arm are accommodated in separate openings. The seals may have secondary features such as ribs to localize sealing action and to improve seal compliance. The dielectric substrate can be a multi-layer substrate or even a two-piece construction wherein the inner piece provides a hermetic seal and the outer seal provides structural support and accommodates the compressible contacts. Additional components, such as a filter capacitor or a printed circuit board, can be added to the interior side of the dielectric substrate. Connector clamping means can be selected from numerous options known, such as screw-clamped covers, clam shell latching lids, spring clips, or cam-actuated covers. As to every element, it may be replaced by one of multiple equivalent alternatives, only some of which are disclosed in the specification.

Thus the scope should be determined, not by the examples or specifics given, but by the appended claims and their legal equivalents.

I claim:

1. An implantable electrical connector assembly for separably connecting at least one multi-conductor implantable lead, having a proximal end with a plurality of lead contacts, to an implantable device, said connector assembly comprising:
   (a) a hermetic electrical feedthrough comprising a housing having inside walls and side walls; at least one dielectric substrate having an exterior side and an interior side; at least one exterior cavity formed by said inside walls and said exterior side of said dielectric substrate; a plurality of conductive feedthrough pins, said feedthrough pins providing pass-through connections from said exterior side of said dielectric substrate to said interior side of said dielectric substrate, each said feedthrough pin having an external end communicating with said feedthrough external cavity;
   (b) a plurality of receptacle contact assemblies, each receptacle contact assembly comprising a receptacle contact and a contact guard, said contact guard having a base and side arms, said side arms having outermost tips; said contact assembly adapted to join and electrically connect to said external end of said feedthrough pin; said receptacle contact having a mid-section and a plurality of resilient contact tines, each contact tine having a mating end; said receptacle contact mid-section joined and electrically connected to said contact guard base, said contact guard providing protection for said receptacle contact by protectively shielding said receptacle contact and limiting unintended excursion of any of said contact tines;
   (c) at least one elastomeric seal having at least one lumen for receiving said proximal end of said multi-conductor lead without significant interference, said seal having a bottom side cooperating with said exterior side of said dielectric substrate, and having a top side; said bottom side having apertures communicating with said lumen so that, after said proximal end of said lead is inserted into said lumen, each lead contact is accessible from said bottom side of said seal for an engagement by said contact tines of said receptacle contact when said connector is mated;
   (d) a connector clamping means comprising a clamping cover and at least one fastener; said clamping cover cooperating with said top side of said seal, said at least one fastener adapted to detachably engage said feedthrough housing, whereby when said clamping means are attached to said feedthrough housing, said cover exerts pressure on said top side of said seal thus completing the engagement of said lead contact with said contact tines and compressing said seal; the compression of said seal causing said seal apertures to be sealed along said exterior side of dielectric substrate and between said lead contacts along said lumen of said seal, thus isolating electrical connections contained within each said seal aperture.

2. The connector of claim 1 wherein said side arms of said contact guard have cutouts, whereby said mating ends of said contact tines pass through said cutouts and are protected therein from unintended access.

3. The connector of claim 1 wherein said outermost tips of said contact guard arms extend beyond said mating ends of said contact tines, thus protecting said mating ends from inadvertent access.

4. The connector of claim 1 wherein said side arms of said contact guard have slots, whereby said contact tines are substantially confined in said slots and are protected therein from unintended access.

5. The connector of claim 1 wherein said mid-section of said receptacle contact and said base of said contact guard have substantially equal widths and are joined together by edge-to-edge welding.

6. The connector of claim 1 wherein said mid-section of said receptacle contact is joined to said base of said contact guard by surface-to-surface welding.

7. The connector of claim 1 wherein said external end of said feedthrough pin is a pin head adapted to locate and join said contact guard of said receptacle contact assembly, said base of said contact guard having a complementary hole profiled and sized for close fit on said pin head, whereby said contact guard is attached to said pin head along corresponding outside edges of said pin head and said hole.

8. The connector assembly of claim 7 wherein said pin head and said hole in said base are circular.

9. The connector assembly of claim 7 wherein said pin head and said hole in said base are oblong.

10. The connector assembly of claim 1 wherein said contact tines are preloaded against said contact guard.

11. The connector of claim 1 wherein said external end of said feedthrough pin is a pin head adapted to locate and join said receptacle contact of said receptacle contact assembly, said mid-section of said receptacle contact having a hole profiled and sized for close fit on said pin head; said receptacle contact attached to said pin head along corresponding outside edges of said pin head and said receptacle contact hole.

12. The connector of claim 1 wherein said external end of said feedthrough pin is a slotted head having a slot adapted to locate and join said contact guard of said receptacle contact assembly, said slot having a width closely matched to the width of said contact guard base, said contact guard attached to said feedthrough pin head along corresponding outside edges of said slot and said contact guard base.

13. The connector of claim 12 wherein said receptacle contact and said contact guard have substantially uniform and equal widths.

14. The connector of claim 12, wherein said contact guard base has a stepped width and said slotted head has flat side faces, said stepped width cooperating with said flat faces of said slotted head to self-align said contact assembly to said slotted head for joining.

15. The connector of claim 12 wherein said mating ends of said contact tines wrap around said outermost tips of said contact guard arms in order to limit unintended excursion of said mating ends.

16. The connector of claim 12 wherein each resilient tine has at least one inflection form.

17. The connector of claim 1 wherein said at least one fastener is a retention clip, said retention clip latching against said undercuts on said side walls of said feedthrough housing.

18. An implantable electrical connector assembly for separably connecting at least one multi-conductor implantable lead, having a proximal end with a plurality of lead contacts, to an implantable device, said connector assembly comprising:

(a) a hermetic electrical feedthrough comprising a housing having inside walls and side walls, at least one dielectric substrate having an exterior side and an interior side; at least one exterior cavity formed by said inside walls and said exterior side of said dielectric substrate; and a plurality of conductive feedthrough pins, said feedthrough pins providing pass-through connections from said exterior side of said dielectric substrate to said interior side of said dielectric substrate, each said feedthrough pin having an integral contact guard communicating to said feedthrough external cavity, the contact guard having a middle section and slotted sides;

(b) a plurality of receptacle contacts, each receptacle contact having a mid-section and a plurality of resilient contact tines, said mid-section of said receptacle contact joined and electrically connected to said contact guard middle section, said contact guard providing protection for said receptacle contact by protectively shielding said receptacle contact within said slotted sides and limiting unintended excursion of any of said contact tines;

(c) at least one elastomeric seal having at least one lumen for receiving said proximal end of said multi-conductor lead without significant interference, said seal having a bottom side cooperating with said exterior side of said dielectric substrate, and having a top side; said bottom side having apertures communicating with said lumen so that, after said proximal end of said lead is inserted into said lumen, each said lead contact is accessible from said bottom side of said seal for an engagement by said contact tines of said receptacle contact when said connector is mated;

d) a connector clamping means comprising a clamping cover and at least one fastener; said clamping cover cooperating with said top side of said seal, said at least one fastener adapted to detachably engage said feedthrough housing, whereby when said clamping means are attached to said feedthrough housing, said cover exerts pressure on said top side of said seal thus completing the engagement of said lead contact with said contact tines and compressing said seal; the compression of said seal causing said seal apertures to be sealed along said exterior side of dielectric substrate and between said lead contacts along said lumen of said seal, thus isolating electrical connections contained within each said seal aperture.

19. The connector of claim 18 wherein said contact guard has a slot on top of said middle section, the width of said slot closely matched to said contact mid-section width so that said receptacle contact can be joined to said contact guard along top edges of said slot.

20. The connector assembly of claim 18 wherein said receptacle contacts have internal preload.

21. The connector of claim 18 wherein said at least one fastener is a retention clip, said retention clip latching against said undercuts on side walls of said feedthrough housing.

* * * * *